United States Patent
Chatelin et al.

[11] Patent Number: 5,897,782
[45] Date of Patent: Apr. 27, 1999

[54] METHOD FOR ADSORBING ANTIMICROBIAL AGENTS CONTAINED IN A BIOLOGICAL FLUID AND APPARATUS FOR CARRYING OUT THIS METHOD

[75] Inventors: Roger Chatelin, Lissieu; Daniel Monget, Saint Sorlin en Bugey; Thierry Pollet, Ecully; Catherine Fitzer-Couturier, Dagneux; Patrick Gayrine, Ecully, all of France

[73] Assignees: Institut Textile de France; Bio Merieux, Marcy L'Etoile, both of France

[21] Appl. No.: 08/776,998

[22] PCT Filed: Jun. 22, 1996

[86] PCT No.: PCT/FR96/00955

§ 371 Date: Feb. 19, 1997

§ 102(e) Date: Feb. 19, 1997

[87] PCT Pub. No.: WO97/00970

PCT Pub. Date: Jan. 9, 1997

[30] Foreign Application Priority Data

Jun. 22, 1995 [FR] France .................................. 95 07739

[51] Int. Cl.$^6$ .................................................. B01D 15/00
[52] U.S. Cl. ...................... 210/694; 210/435; 210/502.1; 210/503; 210/505
[58] Field of Search .................................. 210/645, 660, 210/694, 767, 435, 446, 453, 456, 464, 494.1, 502.1, 503, 505, 507, 508, 509, 321.79, 321.8, 416.1, 321.88, 321.89; 422/101, 102; 502/401, 402, 403; 604/4, 5, 7, 28, 68

[56] References Cited

U.S. PATENT DOCUMENTS

| | | | |
|---|---|---|---|
| 3,187,389 | 6/1965 | Weichselbaum | 210/448 |
| 3,570,673 | 3/1971 | Dutz et al. | 210/500.1 |
| 3,972,818 | 8/1976 | Bokros | 210/505 |
| 4,174,277 | 11/1979 | Melnick et al. | 422/101 |
| 4,181,513 | 1/1980 | Fukuda et al. | 55/382 |
| 4,565,727 | 1/1986 | Giglia et al. | 210/508 |
| 4,696,742 | 9/1987 | Shimazaki | 210/505 |
| 4,820,276 | 4/1989 | Moreno | 604/190 |
| 4,944,884 | 7/1990 | Naoi | 210/692 |
| 5,089,135 | 2/1992 | Yoneyama et al. | 210/500.23 |
| 5,314,855 | 5/1994 | Thorpe et al. | 502/402 |
| 5,518,620 | 5/1996 | Eguchi et al. | 210/651 |
| 5,660,731 | 8/1997 | Piechocki et al. | 210/694 |

FOREIGN PATENT DOCUMENTS

| | | |
|---|---|---|
| 0105579 | 4/1984 | European Pat. Off. . |
| 0231105 | 8/1987 | European Pat. Off. . |
| 0517189 | 12/1992 | European Pat. Off. . |
| 0597542 | 5/1994 | European Pat. Off. . |
| 0628346 | 12/1994 | European Pat. Off. . |
| 2543849 | 10/1984 | France . |

*Primary Examiner*—John Kim
*Attorney, Agent, or Firm*—Wall Marjama Bilinski & Burr

[57] ABSTRACT

This invention relates to adsorbing antimicrobial agents contained in a biological fluid by passing the fluid over and through a fibrous material that is free of binding agents and is formed of activated carbon fibers.

9 Claims, 2 Drawing Sheets

METHOD FOR ADSORBING ANTIMICROBIAL AGENTS CONTAINED IN A BIOLOGICAL FLUID AND APPARATUS FOR CARRYING OUT THIS METHOD

BACKGROUND OF THE INVENTION

The invention relates to a method for adsorbing or removing antimicrobial agents, also referred to as "inhibitors" or "inhibitory agents", contained in a biological fluid such as, in particular, blood; it also relates to. an apparatus for carrying out this method.

In the description and in the claims, the terms "antimicrobial agents", "inhibitory agents" or "inhibitors" are used to denote any agent intended for preventing the proliferation of microbes or pathogenic microorganisms, such as, for example, antibiotics, antifungals, antivirals and antiseptics.

The term "biological fluid" is used to denote any fluid containing living matter, such as plasma, cerebrospinal fluid, urine, synovial fluid and, preferably, blood.

In the remainder of the description, the invention will be essentially illustrated by its preferred application to blood.

For numerous applications, it is well known to adsorb the antibiotics contained in blood, in particular for the purpose of removing them in order thereafter to analyze the blood which has been purged in this way.

The detection of pathogenic microorganisms in biological fluids must be performed in the shortest possible time, in particular in. the case of septicemia for which the mortality remains high in spite of the broad range of antibiotics which are available to doctors. In order to increase sick individuals' chances of survival, practitioners often administer an antibiotic or mixture of antibiotics to the patients. It is, however, important to determine a suitable antibiotic therapy as soon as possible. Unfortunately, the isolation and rapid characterization of infectious microorganisms is difficult when the blood samples to be analyzed contain inhibitory agents such as antibiotics, which often slow down or even abolish microbial growth.

The same applies to the microorganisms responsible for meningitis, whose presence in the cerebrospinal fluid must be detected with the utmost speed. Here too, the presence of antibiotics may interfere with this detection.

Bacteriuria may also be difficult to diagnose when the patient is subjected to antibiotic therapy and excretes antibiotics in the urine. Frequently, the isolation of infectious microorganisms can be negative.

In order to remedy these drawbacks and improve the detection of the microbes and their isolation in samples of biological fluids from patients on antibiotic therapy, several methods have already been proposed which are directed towards removing or neutralizing the antibodies present in the blood before analyzing the blood which has been purged in this way.

In the first place, the proposal has been made to pass the blood over ion exchange resins or adsorbent polymers. For this purpose, the blood drawn from the patient is placed in a first bottle containing such resins or such polymers, and the whole is gently agitated for a suitable time. A volume of this purged blood is then transferred to a second bottle containing the culture medium which is suitable for the growth of the microorganisms possibly present. This technique permits good adsorption of most antibiotics. However, since the adsorbent materials take the form of granules or powder included in the first bottles, this technique separate from the drawing of the blood itself necessitates an additional step of taking up and transfering the blood which has been purged in this way, which is expensive and sometimes of questionable efficiency inasmuch as not all the antibiotics present are adsorbed, and sometimes gives rise to releases with the passage of time.

The suggestion has also been made to employ resins contained directly in analysis bottles containing the culture medium. Here too, risks of release of the inhibitory agents with the passage of time and risks of inhibition due to the very composition of the resins are observed.

In the document EP-A-0,597,542 corresponding to the document U.S. Pat. No. 5,314,855, an adsorbent composition has been proposed consisting of a mixture of active charcoal, fuller's earth, a powdered anion exchange resin and a mixture of cationic and anionic polyelectrolytes. This technique has, however, the same drawbacks as those of ion exchange resins. In effect, in this method, the blood is first drawn and then, away from the place where it has been drawn, is simultaneously treated and analyzed in the analysis bottle containing a suitable culture broth and the adsorbent composition.

In addition, since the antibiotic remains in the mixture, as before, risks of release are observed. Moreover, the presence of active charcoal in suspension interferes with the analysis in the bottle, since this charcoal can adsorb other compounds, in particular factors needed for the growth of the microorganisms, thereby inducing false-negative results. In addition, the exchange surface areas often prove insufficient for adsorbing in their entirety the inhibitory agents present in the drawn sample, so that the filled bottle must be agitated significantly in order to obtain a good exchange efficiency. Lastly, as a result of the presence of active charcoal, this technique can make it difficult to carry out further examinations such as, in particular, direct reading by eye or under a microscope.

SUMMARY OF THE INVENTION

The invention remedies these drawbacks.

It relates to a method of adsorption, in particular of antimicrobial agents contained in a biological fluid, which may be carried out immediately following and in continuous fashion with the drawing of said biological fluid and before it is cultured, thereby avoiding any interference and favoring the growth of the microorganisms in the sample to be analyzed.

This assumes very special importance since, when samples are drawn and then stored in an incubator for several hours for the purpose of carrying out culturing and subsequent analysis, an inhibitory action of the antibiotic agents on the microorganisms in the sample may develop. As before, this can induce false-negative results.

According to the method of the invention for adsorbing antimicrobial agents contained in a biological fluid, by passing this fluid over a filtering and adsorbing compound, said compound takes the form of a fibrous textile material based on fibers of activated carbon and which is free from any binding agent.

In other words, the invention consists in adsorbing the antimicrobial or inhibitory agents contained in a biological fluid, no longer by means of an exchange resin or a composition based on active charcoal and fuller's earth in granular or powder form, but by passing a blood sample, immediately after and in continuous fashion with the drawing of the fluid, over a fibrous textile material based on fibers of activated carbon whose coherency is effected only by their interlacing and hence in the absence of any binding agent, before introducing the blood which has been purged in this way into the bottles containing the culture medium, for growth of the microorganisms liable to be present.

As is known, carbon fibers are materials which display advantageous mechanical properties in combination with a low density, which enable them to be used in the widest variety of textile forms, such as filaments, fibers or two- or three-dimensional fabrics or braids. Most generally, these fibers are manufactured by pyrolysis of a precursor, in particular based on natural or artificial cellulose fibers or even on synthetic fibers (acrylic fibers). Since these carbon fibers are well known, no purpose is served by describing them here in detail.

It was observed altogether surprisingly that, in order to obtain the desired result, namely the adsorption of antimicrobial agents, it is important for these carbon fibers to have been activated, that is to say to have undergone a controlled oxidation, which causes an attack at the surface of and deep within each of the fibers, which then become more or less porous. More or less radial channels capable of adsorbing undesirable molecules then develop at the surface and in the core of these fibers. Thus, the finer the pores, the larger the specific surface area and the greater the efficiency of adsorption. Similarly, it is possible to modify the conditions of oxidation of the fibers by varying, in particular, the temperature of treatment, this being done so as to control the size of the pores developed at the surface and in the core of the fibers, and consequently their selectivity.

In practice, the oxidation temperature is adjusted in such a way as to give rise, in the core and at the surface of the fibers, to small pores thus retaining the undesirable molecules while allowing the large molecules to pass by.

Most generally, the activation of the carbon fibers is performed by controlled oxidation at a temperature of between 800 and 1000° C. in an inert atmosphere.

Fibers of activated carbon are well known in the field of deodorizing or of purification, in particular of gases. It is surprising that the use of these fibers of activated carbon also enables such an efficiency and speed of adsorption to be obtained, whereas particles of activated charcoal or fibers of unactivated carbon do not enable comparable results to be obtained and, most particularly, present real difficulties of implementation. As a result, an expert in the field of the analysis of microbiological agents, aware of the abovementioned drawbacks of adsorption onto carbon fibers or onto particles of activated charcoal, was dissuaded from employing specific carbon fibers, namely fibers of activated carbon.

Moreover, the coherency of fibers of activated carbon is effected by their interlacing, this taking place in the absence of any binding agent, permitting a surprising. increase in the filtration and adsorption capacity of the carbon fibers.

As a result of the combined effect of speed and efficiency, the method according to the invention becomes compatible with the rates of drawing of the biological fluid, and may hence be performed simultaneously with the drawing itself and be incorporated or integrated in continuous fashion in the actual process of drawing, more precisely between the patient and outside of the analytical environment, thereby avoiding any interference with the subsequent analyses.

Thus, the selection of fibers of activated carbon permits the adsorption of antimicrobial or inhibitory agents immediately following and in continuous fashion with the drawing of the fluid, which could not be done hitherto. This is reflected in a simplicity in the implementation and a greater reliability of the results obtained.

The fibrous material characteristic of the invention may take the most diverse forms. For example, a bundle of parallel filaments may be employed. It is also possible to use discontinuous fibers, surfaces or textile fabrics: woven, braided, knitted, nonwoven, two- or three-dimensional, felt, wadding, netting, velvet, and the like.

It is important for the specific surface area of the fibers (or filaments) to be high. It was found that good results were obtained with specific surface areas greater than 500 $m^2/g$, and preferably greater than 1000 $m^2/g$, for a diameter of the fibers (or filaments) of between five and fifty micrometers, and preferably in the region of ten micrometers.

It is important for the organization of the fibrous material in the device to permit the passage of large molecules or of microorganisms in the biological fluid to be analyzed, but to enable smaller molecules such as antimicrobial or inhibitory agents to be retained.

The liquid to be adsorbed may thus be passed in contact with the fibers or filaments organized in the forms or surfaces mentioned above. Thus, the fibrous material makes it possible, on the one hand, by the microporous structure of the fibers of activated carbon, to effect a good adsorption of antimicrobial agents, and on the other hand, as a result of the structure of the material itself, to conduct a selective separation of the constituents of the fluid to be analyzed.

Depending on the form taken by the fibrous material, contact with the biological fluid takes place essentially at the surface and/or in the core of the material.

It was observed that good results are obtained by running the biological fluid through a flexible sampling catheter inside which a bundle of a few (from five to fifty) parallel filaments of fibers of activated carbon has been inserted.

In another embodiment, the adsorbing compound according to the invention is held in a module or several superposed modules which is/are interposed in the pathway of flow of a flexible catheter.

Good results are also obtained by running the biological fluid through a syringe, the cylindrical barrel of which contains an adsorbing compound of the type described in the invention.

The efficiency of the contact and exchange between the biological fluid and the filtering and adsorbing compound according to the invention may advantageously be enhanced by arranging a distributing device upstream of said compound relative to the direction of flow of the biological fluid, whose function consists in distributing the stream of biological fluid over the whole of the surface of said filtering and adsorbing compound.

The flow may also take place through three-dimensional fabrics in the form of twists and turns, zig-zags, spirals or the like in order to increase the distance traveled and thereby the surface area and the duration, as well as the efficiency of the contact and exchange. Composite materials with an open structure may also be used (loose-stitched knitted fabric, open-pore cellular structure).

The choice of the form taken by the actual fibrous material takes account essentially of the fluid to be treated, the rate of flow and the antimicrobial agents to be adsorbed.

The fluid is passed over the characteristic fibrous material based on fibers of activated carbon by any known means. Gravity may be employed. Preferably, the fluid is passed through under slightly reduced pressure, such as by suction, sufficient to draw the fluid, in a similar manner to the drawing of biological fluid from a patient.

The invention also relates to an apparatus for carrying out this method. This apparatus comprises:
- a means for drawing a biological fluid;
- a pipe, connected on one side to the drawing means and on the other side to a vessel designed to receive the extracted biological fluid to be analyzed;
- a means designed to initiate the drawing of the biological fluid.

It is characterized in that the pipe possesses within it, and over at least part of its length, a fibrous material based on fibers of activated carbon, in contact with which the extracted biological fluid passes as the drawing proceeds.

In practice:
- the means for drawing the biological fluid is, depending on the application envisaged, either a needle (blood) or a tube (urine);
- the pipe is a flexible catheter made of a biocompatible material, for example of plastic;
- the vessel is combined with the means for initiating the drawing; this can be, for example, a bottle under partial vacuum or a pump barrel.

In another embodiment, the biological fluid is run through one or more modules, each module defining an internal cavity and possessing, on each side of said cavity, two openings designed to be fitted, respectively, to an inflow pipe and to an outflow pipe for biological fluid.

In the case of a plurality of modules, the latter are superposed, and in all cases they each contain a fibrous textile material based on activated carbon occupying the whole of the available volume over a specified thickness.

To optimize the distribution of the stream of biological fluid over the surface of the fibrous textile material, each module advantageously contains a distributing device arranged at least upstream of the fibrous textile material, relative to the direction of flow of the biological fluid.

Preferably, each module is of circular transverse section, and the fibrous textile material based on activated carbon takes the form of a disk of diameter slightly larger than the internal diameter of the cavity defined by the module, the disk occupying the whole of the available volume over a specified thickness.

The term "diameter slightly larger" is used to denote a diameter 1 to 2 millimeters larger than the internal diameter of the module.

Lastly, the biological fluid may also be filtered by means of a syringe, the cylindrical barrel of which contains a fibrous textile material according to the invention occupying the whole of the available volume over a specified thickness. In this embodiment, the fluid to be treated is introduced into the barrel of the syringe with the plunger retracted, and it then travels through the fibrous textile material, after the plunger has been brought into position and shifted, before being discharged through the needle attachment tip or the needle itself.

In the description and in the claims, the expression, "occupying the whole of the available volume over a specified thickness" is understood to mean the available volume inside the module or the barrel of the syringe, defined on the one hand by the internal side walls, respectively, of the module and of the syringe, and on the other hand by the specified thickness conferred on said material, such that there are no gaps between the filtering and adsorbing material and said walls.

BRIEF DESCRIPTION OF THE DRAWINGS

The manner in which the invention may be implemented and the advantages stemming therefrom will become more clearly apparent from the examples of implementation which follow with the support of the attached figures.

DESCRIPTION OF THE INVENTION

Figure 1:
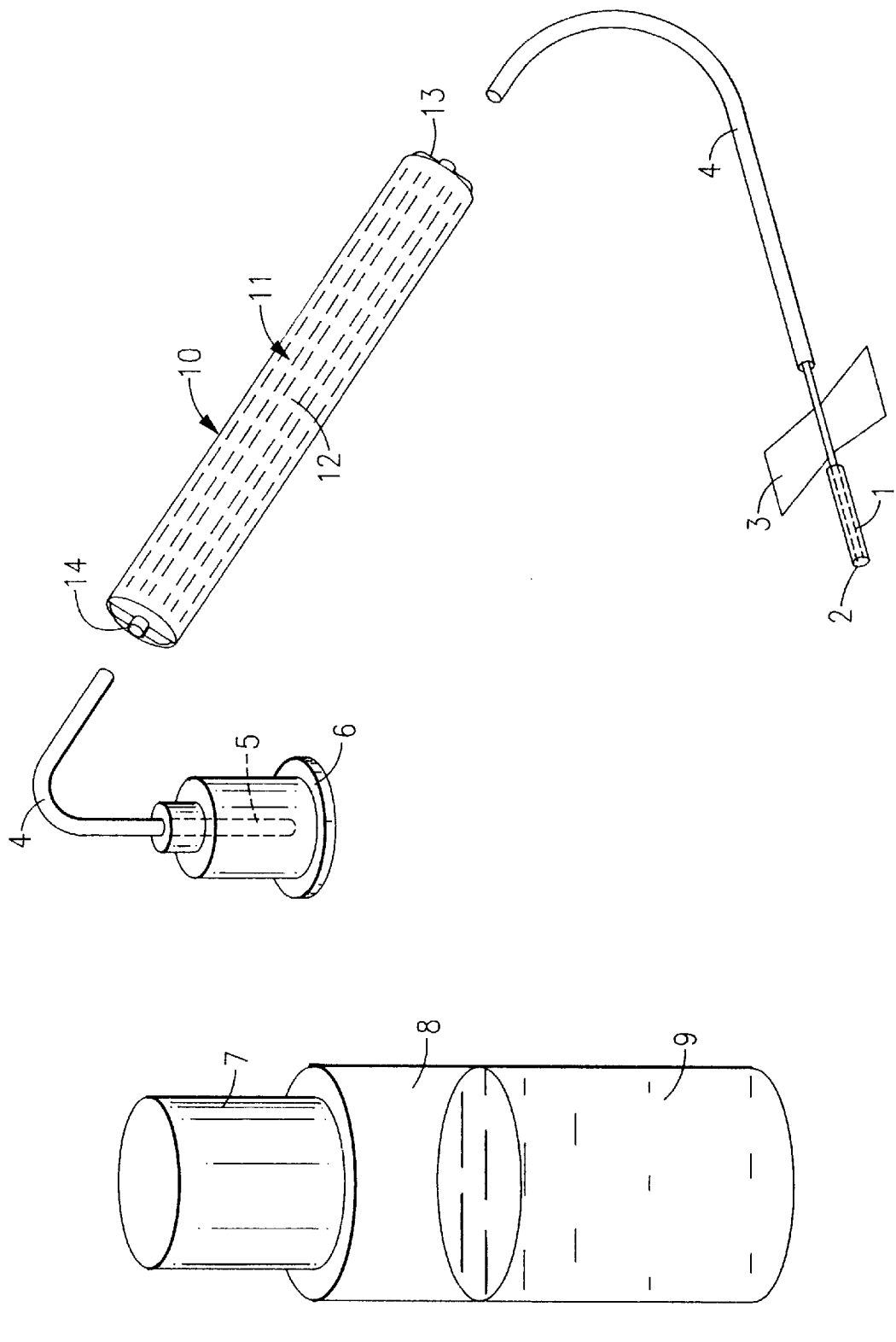
FIG. 1 is a diagrammatic representation of a piece of equipment according to the invention.

A drawing and treatment apparatus for carrying out the invention comprises (see FIG. 1) in a known manner, respectively, a needle (1) with tabs (3), placed in a known manner in a protecting tube (2). The end of the needle (1) is connected to a flexible catheter (4) connected at its other end to a needle (5) surrounded by a protecting cap (6). This cap (6) is designed to become positioned over a stopper (7), generally made of rubber, of a bottle (8) containing a culture broth (9). The interior of the bottle (8) is at a reduced pressure corresponding to a few hundred Pa.

According to the invention, the catheter (4) is interrupted by a tube (10) with which it communicates, said tube containing a bundle (11) composed of a plurality of parallel filaments (12) of activated carbon ten micrometers in diameter. This tube (10) is connected in a known manner by its two ends (13, 14) to the catheter (4).

Figure 2:
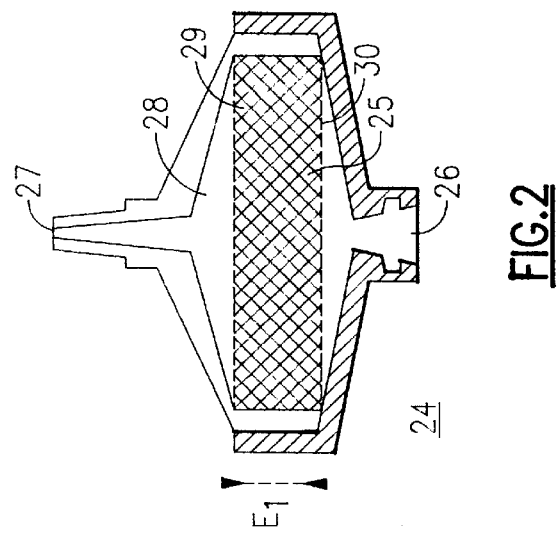
FIG. 2 is a transverse section of a module according to the invention.

Advantageously, the tube (10) is replaced by a module (24) provided with two openings, a female opening (26) receiving a biological fluid inflow pipe, and a male opening, prolonged in the form of a channel (27), designed to be fitted to a biological fluid outflow pipe (see FIG. 2), said biological fluid outflow pipe being connected to a vessel designed to receive the extracted biological fluid to be analyzed. This module, of circular transverse section, delimits a cavity (28) containing two distributing devices (29, 30) arranged on each side of a fibrous textile material based on fibers of activated carbon, occupying the whole of the available volume over a specified thickness (E1), the distributing devices being designed to distribute the stream of biological fluid over the whole of the textile material. This molecule has the advantage of being able to be produced in large quantities and of being able to be fitted universally to standard sampling catheters. In other words, this device enables the blood to be purged immediately at the place of drawing, in a simple and inexpensive manner.

In an embodiment which is not shown, a series of modules provided, as above, with a male upper opening and a female lower opening, which openings are designed to be fitted, respectively, to the openings of the adjacent modules, are superposed. The openings of the modules thus defined are also capable of being fitted to the biological fluid inflow and outflow pipes.

When it is desired to analyze a patient's blood, the needle (1) is inserted into a vein. When the blood appears in the catheter (4), the cap (5) is placed over the stopper (7) of the bottle (8), pushing the needle (5) through the stopper (7). The reduced pressure in the bottle (8) sucks the blood into the circuit (4, 10), which then flows into the bottle (8) where it reacts with the broth (9).

During this drawing of blood, the latter flows over and through the bundle (11) of parallel filaments of activated carbon, which then retain the antimicrobial or inhibitory agents, and the blood which has been purged in this way is then brought into contact with the appropriate culture medium in order to permit the growth of the microorganisms possibly present in the sample.

Figure 3:
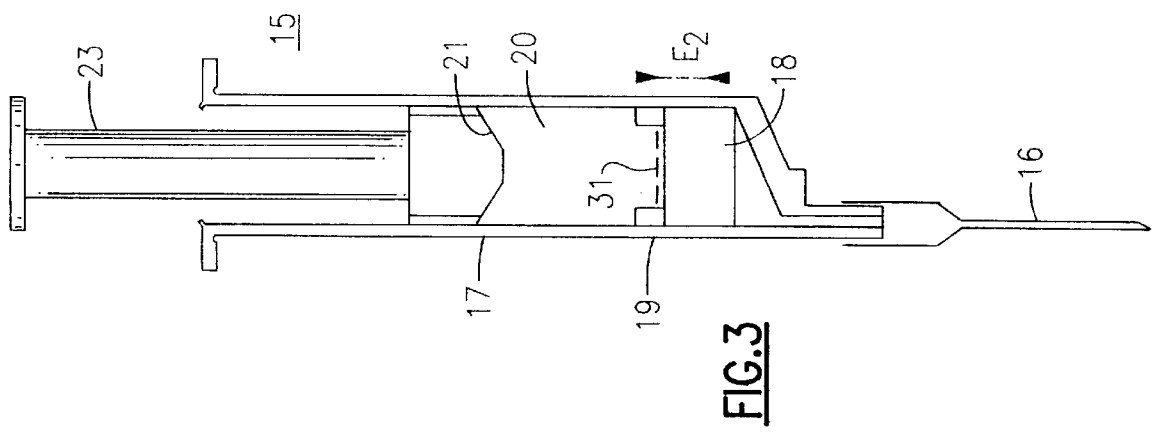
FIG. 3 is a diagrammatic representation of a syringe according to the invention.

In another embodiment (FIG. 3), the apparatus consists of a syringe (15) comprising, in a known manner, a needle (16), a cylindrical barrel (17) and a plunger (23). The barrel (17) contains, in the part immediately adjacent to the needle fitting channel, a felt inserted forcibly, occupying the whole of the available volume over a specified thickness (E2), composed of a plurality of parallel filaments of activated carbon (18), held by a retaining ring (19) which prevents any movement of the felt in the syringe as well as any preferential flow, in particular along the walls of the barrel. Furthermore, the space (20) left between the adsorbing material of the invention (18) and the end (21) of the plunger receives the sample to be treated. Arranged upstream of the felt (18), relative to the direction of flow of the biological fluid, is a grid (31) designed to distribute the stream of biological fluid over the whole of the surface of said felt.

Thus, when it is desired to analyze a patient's blood, the plunger (23) of the syringe (15) is withdrawn and the sample to be analyzed is placed in the space (20). The plunger is then reintroduced into the syringe and thereafter, by shifting the plunger, the fluid is forced to pass through the adsorbing material (18). The sample is then filtered and thereafter discharged through the needle fitting channel or through the needle itself, in order to be brought into contact with a suitable culture medium in an independent vessel.

Validation of the method of the invention

The absorption capacity in respect of antibiotics is determined by the conventional agar diffusion technique described below.

A blood sample is drawn from a normal, healthy patient, that is to say one free from antibiotic. A predetermined amount of a major antibiotic in current use is then added to this blood. A reference sample is thereby obtained, hereinafter designated S-ATB.

Using a syringe, a part of the sample of this S-ATB blood is drawn up and introduced into the catheter (4) in order to pass it over the fibrous material (11).

Both the purged blood sample and the reference sample are collected in the broth (9). The red cells are then allowed to sediment for thirty minutes in conical-bottomed tubes. A bacterial assay of the antibiotics is then performed.

In a known manner, a fraction of blood to be analyzed is drawn up and applied to a paper disk which is dried. This disk is then placed in a Petri dish and, on the surface of the latter, bacteria sensitive to the antimicrobial agent which it is desired to detect and quantify are deposited. The Petri dish is then placed in an incubator. During the incubation, the antimicrobial agent, if present, diffuses into the agar and an inhibition diameter is obtained after twenty-four hours.

The diameter obtained is then compared with a reference series in order to be able to quantify the amount of inhibitors present, before and after the treatment according to the invention.

EXAMPLE 1

In this example, the bundle (11) is composed of eight parallel strands thirty centimeters in length of fibers of activated carbon ten micrometers in diameter and possessing a specific surface area of 1500 m²/g. The internal diameter of the tube (10) is 3.10 mm.

The time taken for a sample of five milliliters of blood to pass through is set by the reduced pressure in the bottle (8), or by the reduced pressure caused by a plunger, at between 15 and 45 seconds, to correspond to the time taken in drawing a normal blood sample from a patient.

The amount of antibiotics adsorbed onto the fibrous material (11, 12) is measured by conventional microbiological assay, by agar diffusion in Petri dishes. The percentage of inhibitors adsorbed onto the fibrous material is equal to:

reference value−test value/reference value× 100

The results are collated in Table I below.

EXAMPLE 2

The previous example is repeated, replacing the bundle (12) by a bundle of twenty-four strands identical to the eight strands of Example 1.

The results are collated in Table I below.

|  | Netilmicin | Vancomycin | Pefloxacin | Amoxycillin |
| --- | --- | --- | --- | --- |
| Concentration in mg/l of the antibiotic agent in the sample | 40 | 40 | 20 | 80 |
| Example 1 | 22 | 3 | 25 | 61 |
| Example 2 | 80 | 39 | 50 | 79 |

The figures shown correspond to percentage adsorption values for the characteristic fibrous material (11, 12).

EXAMPLE 3

Example 1 is repeated, replacing the fibers of activated carbon (12) characteristic of the invention by carbon fibers of the same linear density and same length, but unactivated.

No adsorption is observed.

EXAMPLE 4

Example 1 is repeated, replacing the fibers of activated carbon by particles of active charcoal.

No significant adsorption is observed.

As is apparent from the foregoing description, the method, equipment and device according to the invention enable the biological fluid to be purged as it is being drawn.

Accordingly, the invention may be used successfully for the removal of antimicrobial or inhibitory agents from plasma, cerebrospinal fluid, urine, synovial fluid and, most particularly, blood.

We claim:

1. A method for adsorbing antimicrobial agents contained in a biological fluid that includes the steps of providing a filtering and adsorbing compound of a fibrous textile material, said material being free of binding agents, and its fibers being formed of activated carbon, said carbon fibers in parallel alignment in a bundle; and passing a biological fluid over and through said material whereby antimicrobial agents in the fluid are adsorbed by the textile material.

2. The method of claim 1 wherein the activated carbon fibers have a diameter of between five and fifty micrometers.

3. The method according to claim 1 wherein the specific surface area of each fiber is greater than 500 square meters per gram.

4. The method according to claim 1 wherein said fibrous material is selected from the group consisting of woven and non-woven braided, two and three dimensional braided knotted, felt, wadding, netting and velvet fabric.

5. The method of claim 1 wherein said biological fluid is blood.

6. A method of adsorbing antimicrobial agents contained in a biological fluid that comprises:

providing a filtering and adsorbing fibrous material that is free of binding agents and the fibers of which are formed of carbon;

activating said fibers by subjecting said fibers to a controlled oxidation to produce radially disposed pores in said fibers, said pore sizes being less than the molecule size of a biological fluid being treated;

passing said biological fluid over and through said fibrous material whereby antimicrobial agents are adsorbed by said fibrous material;

forming said fibrous material of fibers that are between five and fifty micrometers in diameter and having specific surface area greater than 500 square meters per gram; and, aligning the fibers in parallel rows.

7. Apparatus for adsorbing antimicrobial agents contained in a biological fluid that includes means for drawing a biological fluid, a pipe connected at one end to said drawing means and at the other end to a vessel for receiving said biological fluid being drawn, and said pipe further containing an adsorbing and filtering means containing a fibrous material that is free of binding agents and the fibers of which are formed of activated carbon for adsorbing anti-microbial agents in said biological fluid that is being drawn through said pipe, and wherein said carbon fibers are in parallel alignment in a bundle.

8. The apparatus of claim 7 wherein said pipe is a flexible catheter and the biological fluid is blood.

9. The apparatus of claim 7 wherein said vessel is a bottle, the interior of which is at a pressure less than atmospheric pressure.

* * * * *

UNITED STATES PATENT AND TRADEMARK OFFICE
CERTIFICATE OF CORRECTION

PATENT NO. : 5,897,782
DATED      : April 27, 1999
INVENTOR(S): Roger Chatelin et al.

It is certified that error appears in the above—identified patent and that said Letters Patent is hereby corrected as shown below:

On the title page: ITEM:

[22]  PCT Filed: please delete "June 22, 1996" and insert --June 20, 1996 --

Signed and Sealed this

Fourteenth Day of September, 1999

Attest:

Q. TODD DICKINSON

*Attesting Officer*   *Acting Commissioner of Patents and Trademarks*